US010383334B2

(12) United States Patent
Mertoglu et al.

(10) Patent No.: US 10,383,334 B2
(45) Date of Patent: Aug. 20, 2019

(54) EMULSIFIABLE CONCENTRATE COMPRISING PESTICIDE, FATTY AMIDE AND LACTAMIDE

(71) Applicant: BASF AGRO B.V., Arnhem (NL)

(72) Inventors: Murat Mertoglu, Sao Paulo (BR); Stefan Bechtel, Schwegenheim (DE); Natascha Annawald, Schifferstadt (DE); Marcus Annawald, Schifferstadt (DE)

(73) Assignee: BASF Agro B.V., Arnhem (NL)

( * ) Notice: Subject to any disclaimer, the term of this patent is extended or adjusted under 35 U.S.C. 154(b) by 0 days.

(21) Appl. No.: 15/118,718

(22) PCT Filed: Feb. 10, 2015

(86) PCT No.: PCT/EP2015/052695
§ 371 (c)(1),
(2) Date: Aug. 12, 2016

(87) PCT Pub. No.: WO2015/121219
PCT Pub. Date: Aug. 20, 2015

(65) Prior Publication Data
US 2017/0064959 A1 Mar. 9, 2017

(30) Foreign Application Priority Data

Feb. 14, 2014 (EP) .................................... 14155251

(51) Int. Cl.
A01N 25/02 (2006.01)
A01N 25/04 (2006.01)
A01N 43/56 (2006.01)
A01N 47/24 (2006.01)
A01N 43/653 (2006.01)

(52) U.S. Cl.
CPC ........... *A01N 43/653* (2013.01); *A01N 25/02* (2013.01); *A01N 25/04* (2013.01); *A01N 43/56* (2013.01)

(58) Field of Classification Search
CPC ...... A01N 43/56; A01N 43/653; A01N 47/24; A01N 25/02; A01N 25/04
See application file for complete search history.

(56) References Cited

U.S. PATENT DOCUMENTS

| 2007/0270612 | A1 | 11/2007 | Pompeo et al. | |
|---|---|---|---|---|
| 2009/0227453 | A1 | 9/2009 | Bell et al. | |
| 2011/0190129 | A1* | 8/2011 | Bell | A01N 25/02 504/105 |
| 2011/0230437 | A1 | 9/2011 | Bell et al. | |
| 2013/0037749 | A1* | 2/2013 | Hailu | C11D 1/008 252/364 |
| 2013/0210627 | A1 | 8/2013 | Miln et al. | |

FOREIGN PATENT DOCUMENTS

| DE | 4003180 | 8/1991 |
|---|---|---|
| EP | 0113640 | 7/1984 |
| EP | 0126430 | 11/1984 |
| EP | 0275955 | 7/1988 |
| WO | WO-2007/107745 | 9/2007 |
| WO | WO-2009/027626 | 3/2009 |
| WO | WO-2011/082162 | 7/2011 |
| WO | WO 2011/085310 | * 7/2011 |
| WO | WO-2013/007767 | 1/2013 |
| WO | WO-2013/010862 | 1/2013 |
| WO | WO-2013/010885 | 1/2013 |
| WO | WO-2013/010894 | 1/2013 |
| WO | WO-2012/024083 | 2/2013 |
| WO | WO-2013/024075 | 2/2013 |
| WO | WO-2013/024076 | 2/2013 |
| WO | WO-2013/024077 | 2/2013 |
| WO | WO-2013/024080 | 2/2013 |
| WO | WO-2013/024081 | 2/2013 |
| WO | WO-2013/024082 | 2/2013 |
| WO | WO-2013/024083 | 2/2013 |
| WO | WO-2013/087416 | 6/2013 |
| WO | WO-2013/149856 | 10/2013 |
| WO | WO-2013/149925 | 10/2013 |
| WO | WO-2013/156249 | 10/2013 |

(Continued)

OTHER PUBLICATIONS

Yu et al., "Synthesis and Fungicidal Evaluation of 2-Arylphenyl Ether-3-(1H-1,2,4-triazol-1-yl)propan-2-ol Derivatives," J. Agric. Food Chem., 2009, vol. 57, pp. 4854-4860.
International Search Report for PCT/EP2015/052695 dated Mar. 17, 2015.
International Preliminary Report on Patentability for PCT/EP2015/052695 dated Aug. 16, 2016.
Office Action, issued in co-pending U.S. Appl. No. 15/118,680, dated Jun. 27, 2017.
Office Action, issued in co-pending U.S. Appl. No. 15/118,680, dated Dec. 28, 2017.

(Continued)

Primary Examiner — Umamaheswari Ramachandran
(74) Attorney, Agent, or Firm — Brinks Gilson & Lione

(57) ABSTRACT

Subject matter of the present invention is an emulsifiable concentrate comprising a water-insoluble pesticide, an amide of the formula (I) as defined herein, and a lactamide of the formula (II) as defined herein. The invention further relates to a process for the preparation of said concentrate; an emulsion obtainable by mixing water, a water-insoluble pesticide, the amide of the formula (I) and the lactamide of the formula (II); and to a method for controlling phytopathogenic fungi and/or undesired vegetation and/or undesired attack by insects or mites and/or for regulating the growth of plants, where the concentrate or the emulsion is allowed to act on the respective pests, their environment or on the crop plants to be protected from the respective pests, on the soil and/or on undesired plants and/or on the crop plants and/or their environment.

13 Claims, No Drawings

(56) References Cited

FOREIGN PATENT DOCUMENTS

| WO | WO-2013/189745 | 12/2013 |
| WO | WO-2014/128009 | 8/2014 |
| WO | WO-2014/135392 | 9/2014 |
| WO | WO-2014/139805 | 9/2014 |
| WO | WO-2014/180677 | 11/2014 |
| WO | WO-2015/003908 | 1/2015 |
| WO | WO-2015/071139 | 5/2015 |
| WO | WO-2015/121119 | 8/2015 |
| WO | WO-2015/121219 | 8/2015 |

OTHER PUBLICATIONS

Van Nostrand's Scientific Encyclopedia, "Pyrazoles, Pyrazolines, and Pyrazolones," Aug. 2006, retrieved on Dec. 22, 2017 from http://onlinelibrary.wiley.com/doi/10.1002/0471743984.vse8366/pdf.

* cited by examiner

EMULSIFIABLE CONCENTRATE COMPRISING PESTICIDE, FATTY AMIDE AND LACTAMIDE

This application is a National Stage application of International Application No. PCT/EP2015/052695, filed Feb. 10, 2015. This application also claims priority under 35 U.S.C. § 119 to European Patent Application No. 14155251.3, filed Feb. 14, 2014.

Subject matter of the present invention is an emulsifiable concentrate comprising a water-insoluble pesticide, an amide of the formula (I) as defined herein, and a lactamide of the formula (II) as defined herein. The invention further relates to a process for the preparation of said concentrate; an emulsion obtainable by mixing water, a water-insoluble pesticide, the amide of the formula (I) and the lactamide of the formula (II); and to a method for controlling phytopathogenic fungi and/or undesired vegetation and/or undesired attack by insects or mites and/or for regulating the growth of plants, where the concentrate or the emulsion is allowed to act on the respective pests, their environment or on the crop plants to be protected from the respective pests, on the soil and/or on undesired plants and/or on the crop plants and/or their environment. The present invention comprises combinations of preferred features with other preferred features.

Emulsifiable concentrates (also referred to as EC) are widely used formulations in crop protection. The disadvantage of the known emulsifiable concentrates is the poor cold stability, the pronounced tendency to crystallize and the low pesticide concentration.

It was an object of the present invention to provide an emulsifiable concentrate which overcomes these disadvantages.

The object was achieved by an emulsifiable concentrate comprising a water-insoluble pesticide,
an amide of the formula (I)

$$R^1-C(O)N(R^2)_2 \quad (I)$$

where $R^1$ is $C_5$-$C_{19}$-alkyl and $R^2$ is methyl, ethyl, propyl, butyl, or mixtures thereof; and
a lactamide of the formula (II)

$$H_3C-CH(OH)-C(O)N(R^3)_2 \quad (II)$$

where $R^3$ is methyl, ethyl, propyl, butyl, or mixtures thereof.

Usually, an emulsifiable concentrate is taken to mean compositions which form an oil-in-water emulsion upon mixing with water (e.g. in a weight ratio of 1 part concentrate to 99 parts water). The emulsion usually arises spontaneously. The resulting emulsion may have an average droplet size of more than 0.1 µm, preferably more than 0.5 µm, in particular more than 0.8 µm, and most preferred more than 1.1 µm. The average droplet size may be determined by laser diffraction, e.g. with a Malvern Mastersizer 2000.

The concentrate is preferably present as a homogeneous solution. It is usually virtually free from dispersed particles.

Preferred amides of the formula (I) are those in which $R^1$ is $C_7$-$C_{13}$-alkyl (preferably linear) and $R^2$ is methyl. Especially preferred amides of the formula (I) are those in which $R^1$ is $C_7$-$C_{11}$-alkyl and $R^2$ is methyl. In particular, $R^1$ is n-nonyl and $R^2$ is methyl.

According to a further preferred embodiment, the amides of the formula (I) are those in which $R^1$ is $C_8$-$C_{14}$-alkyl, in particular linear $C_8$-$C_{14}$-alkyl. Especially preferred amides of the formula (I) are those in which $R^1$ is $C_7$-$C_{11}$-alkyl, in particular linear $C_7$-$C_{11}$-alkyl. More particularly, $R^1$ is n-nonyl. Furthermore, it is preferred if $R^2$ is methyl.

Mixtures of amides of the formula (I) are also possible, for example mixtures where $R^1$ is $C_7$-$C_{11}$-alkyl and $R^2$ is methyl. Mixtures of amides of the formula (I) comprise in most cases two amides of the formula (I) in an amount of in each case at least 30% by weight (preferably at least 40% by weight) based on the total amount of amides of the formula (I).

The concentrate can comprise up to 75% by weight, preferably not more than 65% by weight and in particular not more than 50% by weight of amide of the formula (I). The concentrate can comprise at least 5% by weight, preferably at least 10% by weight and in particular at least 20% by weight of amide of the formula (I).

It may be suitable, if the concentrate comprises from 5% to 75% by weight, in particular 10% to 75% by weight, more specifically 15% to 75% by weight of the amide of the formula (I).

In a further embodiment, the concentrate comprises from 5% to 65% by weight, in particular 10% to 65% by weight, more specifically 15% to 65% by weight of the amide of the formula (I).

Preferred lactamides of the formula (II) are those in which $R^3$ is methyl. In case $R^3$ is propyl or butyl, these alkyl groups may be linear or branched (e.g. iso-propyl, or tert-butyl).

The concentrate can comprise up to 50% by weight, preferably up to 35% by weight and in particular up to 20% by weight of lactamide of the formula (II). According to a further embodiment, it may be favorable, if the concentrate comprises up to 20% by weight of the lactamide of the formula (I). The concentrate can comprise at least 0.3% by weight, preferably at least 1% by weight and in particular at least 3% by weight of lactamide of the formula (II).

It may be suitable, if the concentrate comprises from 0.3% to 50% by weight, preferably from 1% to 50% by weight, more specifically from 3% to 50% by weight of the lactamide of the formula (II).

In a further embodiment, the concentrate comprises from 0.3% to 30% by weight, preferably from 1% to 30% by weight, more specifically from 3% to 30% by weight of the lactamide of the formula (II).

In still a further embodiment, the concentrate comprises from 0.3% to 20% by weight, preferably from 1% to 20% by weight, more specifically from 3% to 20% by weight of the lactamide of the formula (II).

The weight ratio of the amide of the formula (I) to the lactamide of the formla (II) may be in the range from 1:1 to 20:1, preferably from 2:1 to 15:1, more preferably from 3:1 to 13:1, and in particular from 5:1 to 11:1. In preferred form the weight ratio of the amide of the formula (I) to the lactamide of the formla (II) may be in the range from 1:3 to 20:1, preferably from 1:2 to 15:1, more preferably from 1:1 to 13:1, and in particular from 2:1 to 11:1.

The concentrate may further comprise a hydrocarbon in addition to the amide of formula (I) and the lactamide of formula (II). Suitable hydrocarbon solvents are aliphatic (such as linear or cyclic) or aromatic hydrocarbons. Preferred hydrocarbon solvents are aromatic hydrocarbons. Aromatic hydrocarbons may, besides at least one aromatic hydrocarbon unit, also comprise aliphatic hydrocarbon substituents. In most cases, the hydrocarbon solvent has a solubility in water of not more than 5% by weight, preferably not more than 1% by weight and in particular not more than 0.3% by weight at 20° C. In most cases, the hydrocarbon solvent has a boiling point at 1013 mbar of at least 100° C., preferably at least 150° C. and in particular at least 180° C. Usually, the hydrocarbon solvent comprises only carbon and hydrogen atoms. The hydrocarbon solvent is preferably a $C_6$-$C_{20}$-hydrocarbon, in particular a $C_8$-$C_{16}$-hydrocarbon.

Suitable aromatic hydrocarbons are above all alkyl-substituted aromatics, such as toluene, the xylenes, ethylbenzenes and benzenes having longer-chain alkyl radicals, for example $C_9$-$C_{10}$-dialkyl- and -trialkylbenzenes (for example Solvesso® 100 from Exxon Mobile Europe or Aromatic 100 from Exxon Mobile USA), $C_{10}$-$C_{11}$-alkylbenzenes (for example Solvesso® 150 from Exxon Mobile Europe or Aromatic 150 from Exxon Mobile USA) and alkylnaphthalenes (for example Solvesso® 200 from Exxon Mobile Europe or Aromatic 200 from Exxon Mobile USA). Also suitable are mixtures of the abovementioned aromatics. Preferably, the aromatic hydrocarbon comprises not more than 5% by weight, more preferably not more than 2% by weight and in particular not more than 1% by weight of naphthalene, based on the total weight of the aromatic solvent. Such solvents with a naphthalene content of not more than 1% by weight are commercially available for example from Exxon Mobile Europe with the designation ND (naphthalene depleted), for example Solvesso® 150 ND and Solvesso® 200 ND from Exxon Mobile Europe. Even lower naphthalene contents of not more than 0.1% by weight are present in the products Aromatic 150 ULN and Aromatic 200 ULN from Exxon Mobile USA.

The concentrate can comprise up to 50% by weight, preferably up to 35% by weight and in particular up to 25% by weight of the hydrocarbon. The concentrate can comprise at least 1% by weight, preferably at least 3% by weight and in particular at least 7% by weight of the hydrocarbon.

In a preferred form the concentrate can comprise up to 65% by weight, preferably up to 45% by weight and in particular up to 35% by weight of the hydrocarbon. According to a further embodiment, it may be favorable, if the concentrate comprises up to 40% by weight of the hydrocarbon. In a preferred form the concentrate can comprise at least 0.5% by weight, preferably at least 2% by weight and in particular at least 5% by weight of the hydrocarbon.

It may be suitable, if the concentrate comprises from 0.5% to 65% by weight, preferably from 2% to 65% by weight, more specifically from 5% to 65% by weight of the hydrocarbon.

In a further embodiment, the concentrate comprises from 0.5% to 45% by weight, preferably from 2% to 45% by weight, more specifically from 5% to 45% by weight of the hydrocarbon.

In still a further embodiment, the concentrate comprises from 0.5% to 40% by weight, preferably from 2% to 40% by weight, more specifically from 5% to 40% by weight of the hydrocarbon.

The concentrate can comprise from 10 to 70% by weight of the amide of the formula (I) (e.g. in which $R^1$ is $C_7$-$C_{13}$ and $R^2$ is methyl), 0.3 to 35% by weight of the lactamide of the formula (I) (e.g. in which $R^3$ is methyl) and optionally 1 to 50% by weight of the hydrocarbon, wherein the amounts of these components adds up to a sum of 10.3 to 95% by weight.

In another form the concentrate can comprise from 15 to 65% by weight of the amide of the formula (I), 1 to 30% by weight of the lactamide of the formula (II), and optionally 5 to 40% by weight of the hydrocarbon, wherein the amounts of these components add up to a sum of 16 to 90% by weight.

Preferably, the concentrate can comprise from 20 to 60% by weight of the amide of the formula (I) (e.g. in which $R^1$ is $C_7$-$C_{13}$ and $R^2$ is methyl), 1 to 25% by weight of the lactamide of the formula (I) (e.g. in which $R^3$ is methyl), and optionally 3 to 35% by weight of the hydrocarbon, wherein the amounts of these components adds up to a sum of 21 to 75% by weight.

In particular, the concentrate can comprise from 25 to 50% by weight of the amide of the formula (I) (e.g. in which $R^1$ is $C_7$-$C_{13}$ and $R^2$ is methyl), 3 to 15% by weight of the lactamide of the formula (I) (e.g. in which $R^3$ is methyl), and optionally 7 to 25% by weight of the hydrocarbon, wherein the amounts of these components adds up to a sum of 28 to 70% by weight.

In most cases, the concentrate is free from water. In another form, the concentrate is essentially or largely, respectively, free from water. It can comprise not more than 3% by weight, preferably not more than 1% by weight of water.

In a specific embodiment, the concentrate may comprise not more than 0.5% by weight of water. In a special form, the concentrate may comprise not more than 0.3% by weight and in particular not more than 0.1% by weight of water.

The concentrate may comprise further solvents (e.g. the organic solvents listed below) in addition the amide of the formula (I), the lactamide of the formula (II) and the hydrocarbon. The concentrate can comprise not more than 30% by weight, preferably not more than 10% by weight. In a particular embodiment, it comprises not more than 1% by weight of the further solvents.

In one particular embodiment, in any one of the embodiments of the inventive concentrate described herein, the pesticide is present in dissolved form, the concentrate is largely free from water and the concentrate present as a homogeneous solution.

The term pesticide refers to at least one active substance selected from the group of the fungicides, insecticides, nematicides, herbicides, safeners, biopesticides and/or growth regulators. Preferred pesticides are fungicides, insecticides, herbicides and growth regulators. Especially preferred pesticides are fungicides. Mixtures of pesticides of two or more of the abovementioned classes may also be used. The skilled worker is familiar with such pesticides, which can be found, for example, in the Pesticide Manual, 16th Ed. (2013), The British Crop Protection Council, London. The following classes A) to K) refer to fungicides.

A) Respiration Inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxy-methyl)-phenyl)-2-methoxyimino-N-methyl-acetamide, pyribencarb, triclopyricarb/chlorodincarb, famoxadone, fenamidone, methyl-N-[2-[(1,4-dimethyl-5-phenyl-pyrazol-3-yl)oxylmethyl]phenyl]-N-methoxy-carbamate, 1-[3-chloro-2-[[1-(4-chlorophenyl)-1H-pyrazol-3-yl]-oxymethyl]phenyl]-4-methyl-tetrazol-5-one, 1-[3-bromo-2-[[0-(4-chlorophenyl)pyrazol-3-yl]oxymethyl]phenyl]-4-methyl-tetrazol-5-one, 1-[2-[[1-(4-chlorophenyl)pyrazol-3-yl]oxymethyl]-3-methyl-phenyl]-4-methyl-tetrazol-5-one, 1-[2-[[1-(4-chlorophenyl)pyrazol-3-yl]-oxymethyl]-3-fluoro-phenyl]-4-methyl-tetrazol-5-one, 1-[2-[[1-(2,4-dichlorophenyl)pyrazol-3-yl]oxymethyl]-3-fluoro-phenyl]-4-methyl-tetrazol-5-one, 1-[2-[[4-(4-chlorophenyl)thiazol-2-yl]oxymethyl-]-3- methyl-phenyl]-4-methyl-tetrazol-5-one, 1-[3-chloro-2-[[4-(p-tolyl)thiazol-2-yl]oxymethyl]phenyl]-4-methyl-tetrazol-5-one, 1-[3-cyclopropyl-2-[[2-methyl-4-(1-methylpyrazol-3-yl)phenoxy]methyl]phenyl]-4-methyl-tetrazol-5-one, 1-[3-difluoromethoxy)-2-[[2-methyl-4-(1-methylpyrazol-3-yl)phenoxy]methyl] phenyl]-4-methyl-tetrazol-5-one, 1-methyl-4-[3-methyl-2-[[2-methyl-4-(1-methylpyrazol-3-yl) phenoxy]methyl]phenyl]tetrazol-5-one, 1-methyl-4-[3-methyl-2-[[1-[3-(trifluoromethyl)phenyl]-ethylideneamino]oxymethyl]phenyl]tetrazol-5-one, (Z,2E)-5-[1-(2,4-dichlorophenyl)pyrazol-3-yl]-oxy-2-methoxyimino-N,3-dimethyl-pent-3-enamide, (Z,2E)-5-[1-(4-chlorophenyl)pyrazol-3-yl]oxy-2-methoxy-imino-N,3-dimethyl-pent-3-enamide, (Z,2E)-5-[1-(4-chloro-2-fluoro-phenyl)pyrazol-3-yl]oxy-2-methoxyimino-N,3-dimethyl-pent-3-enamide;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate, 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methyl-propanoate, (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate;

inhibitors of complex II (e.g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide;

other respiration inhibitors (e.g. complex I, uncouplers): diflumetorim, (5,8-difluoro-quinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazolo, 2-[rel-(2S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pent-3-yn-2-ol, 1-[2-chloro-4-(4-chlorophenoxy)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)propan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-3-methyl-1-(1,2,4-triazol-1-yl)butan-2-ol, 1-[2-[2-chloro-4-(4-chlorophenoxy)phenyl]-2-methoxy-pent-3-ynyl]-1,2,4-triazole, 2-[4-(4-chlorophenoxy)-2-(trifluoromethyl)phenyl]-1-(1,2,4-triazol-1-yl)butan-2-ol, 1-[2-[2-chloro-4-(4-chlorophenoxy)phenyl]-2-cyclopropyl-2-methoxy-ethyl]-1,2,4-triazole, 1-[2-[4-(4-chlorophenoxy)-2-(trifluoromethyl)phenyl]-2-methoxy-propyl]-1,2,4-triazole, 2-[2-chloro-4-(4-chlorophenoxy)phenyl]-3,3-dimethyl-1-(1,2,4-triazol-1-yl)butan-2-ol, 1-[2-[4-(4-chlorophenoxy)-2-(trifluoromethyl)phenyl]-2-cyclopropyl-2-methoxy-ethyl]-1,2,4-triazole, 1-[2-[2-chloro-4-(4-chlorophenoxy)phenyl]-2-methoxy-3,3-dimethyl-butyl]-1,2,4-triazole, 1-[2-[4-(4-chlorophenoxy)-2-(trifluoromethyl)phenyl]-2-methoxy-butyl]1,2,4-triazole, 2-[4-(4-chlorophenoxy)-2-(trifluoromethyl)phenyl]-1-(1,2,4-triazol-1-yl)pent-3-yn-2-ol, 1-[2-[4-(4-chlorophenoxy)-2-(trifluoromethyl)phenyl]-2-methoxy-pent-3-ynyl]-1,2,4-triazole, 2-[4-(4-chlorophenoxy)-2-(trifluoromethyl)phenyl]-1-(1,2,4-triazol-1-yl)but-3-yn-2-ol, 2-[2-chloro-4-(4-chlorophenoxy)phenyl]-1-(1,2,4-triazol-1-yl)propan-2-ol, 2-[2-chloro-4-(4-fluorophenoxy)phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 1-[2-[2-chloro-4-(4-chlorophenoxy)phenyl]-2-methoxy-propyl]-1,2,4-triazole, 1-[2-[2-chloro-4-(4-chlorophenoxy)phenyl]-2-methoxy-butyl]-1,2,4-triazole, 1-[2-[2-chloro-4-(4-chlorophenoxy)phenyl]-2-methoxy-pentyl]-1,2,4-triazole, 2-[2-chloro-4-(4-chlorophenoxy)phenyl]-1,1,1-trifluoro-3-(1,2,4-triazol-1-yl)propan-2-ol, 2-[2-chloro-4-(4-chlorophenoxy)phenyl]-3-fluoro-1-(1,2,4-triazol-1-yl) butan-2-ol hydrochloride, 2-[2-chloro-4-(4-chlorophenoxy)phenyl]-1-(1,2,4-triazol-1-yl)pent-4-yn-2-ol, 2-[2-chloro-4-(4-chlorophenoxy)phenyl]-1-methoxy-3-(1,2,4-triazol-1-yl)propan-2-ol, 2-[2-chloro-4-(4-fluorophenoxy)phenyl]-1-methoxy-3-(1,2,4-triazol-1-yl)propan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol, 2-[2-chloro-4-(4-chlorophenoxy)phenyl]-1-(1,2,4-triazol-1-yl) butan-2-ol, 2-[2-chloro-4-(4-chlorophenoxy)phenyl]-1-(1,2,4-triazol-1-yl)pentan-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;

Delta 14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic Acid Synthesis Inhibitors phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D) Inhibitors of Cell Division and Cytoskeleton tubulin inhibitors, such as benzimidazoles, thiophanates: benomyl, carbendazim, fuberidazole, thiabendazole, thiophanate-methyl; triazolopyrimidines: 5-chloro-7-(4-methyl-piperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of Amino Acid and Protein Synthesis methionine synthesis inhibitors (anilino-pyrimidines): cyprodinil, mepanipyrim, pyrimethanil;

protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors

MAP/histidine kinase inhibitors: fluoroimid, iprodione, procymidone, vinclozolin, fenpiclonil, fludioxonil;

G protein Inhibitors: Quinoxyfen;

G) Lipid and Membrane Synthesis Inhibitors

Phospholipid biosynthesis inhibitors: edifenphos, iprobenfos, pyrazophos, isoprothiolane;

lipid peroxidation: dicloran, quintozene, tecnazene, tolclofos-methyl, biphenyl, chloroneb, etridiazole;

phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;

compounds affecting cell membrane permeability and fatty acides: propamocarb fatty acid amide hydrolase inhibitors: oxathiapiprolin;

H) Inhibitors with Multi Site Action inorganic active substances: Bordeaux mixture, copper acetate, copper hydroxide, copper oxychloride, basic copper sulfate, sulfur;

thio- and dithiocarbamates: ferbam, mancozeb, maneb, metam, metiram, propineb, thiram, zineb, ziram;

organochlorine compounds (e.g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methyl-benzenesulfonamide;

guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I) Cell Wall Synthesis Inhibitors inhibitors of glucan synthesis: validamycin, polyoxin B; melanin synthesis inhibitors: pyroquilon, tricyclazole, carpropamid, dicyclomet, fenoxanil;

J) Plant Defence Inducers acibenzolar-S-methyl, probenazole, isotianil, tiadinil, prohexadione-calcium; phosphonates: fosetyl, fosetyl-aluminum, phosphorous acid and its salts, potassium or sodium bicarbonate;

K) Unknown Mode of Action bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, tolprocarb, oxin-copper, proquinazid, tebufloquin, tecloftalam, triazoxide, 2-butoxy-6-iodo-3-propylchromen-4-one, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, N-(cyclopropylmethoxyimino-(6-difluoro-methoxy-2,3-difluoro-phenyl)-methyl)-2-phenyl acetamide, N'-(4-(4-chloro-3-trifluoroethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, picarbutrazox, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline;

M) Growth Regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinex-apac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, metha-benzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

others: benclothiaz, bifenazate, cartap, flonicamid, pyridalyl, pymetrozine, sulfur, thiocyclam, cyenopyrafen, flupyrazofos, cyflumetofen, amidoflumet, imicyafos, bistrifluron, pyrifluquinazon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] cyclopropaneacetic acid ester.

According to one embodiment, the pesticide is selected from the class B) Sterol biosynthesis inhibitors (SBI fungicides), more particularly selected from C14 demethylase inhibitors (DMI fungicides). In particular, the pesticide is selected from the group of triazole fungicides, more specifically is a compound of the following formula:

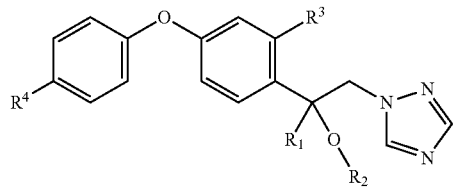

I wherein $R^1$ is $(C_1-C_4)$-alkyl, $(C_3-C_6)$-cycloalkyl, $(C_2-C_4)$-alkinyl or $CH_2OCH_3$, preferably $(C_1-C_4)$-alkyl, $(C_3-C_6)$-cycloalkyl or $(C_2-C_4)$-alkynyl; in particular $CH_3$, $C_2H_5$, n-$(C_3H_7)$, i-$(C_3H_7)$, $C(CH_3)_3$, cyclopropyl or $C\equiv C-CH_3$, more specifically $CH_3$, $C_2H_5$, n-$(C_3H_7)$, i-$(C_3H_7)$, cyclopropyl or $C\equiv C-CH_3$;

$R^2$ is hydrogen, $(C_1-C_3)$-alkyl, $(C_2-C_4)$-alkenyl or $(C_2-C_4)$-alkynyl, in particular hydrogen, $CH_3$, $C_2H_5$, n-$(C_3H_7)$, i-$(C_3H_7)$, $CH_2CH=CH_2$ (allyl), $CH_2C(CH_3)=CH_2$ or $CH_2C\equiv CH$;

$R^3$ is Cl or $CF_3$; and $R^4$ is Cl.

According to one further particular embodiment, the pesticide is selected from the triazoles I-1 to I-31:

compound I-1 2-[2-chloro-4-(4-chlorophenoxy)phenyl]-1-(1,2,4-triazol-1-yl)pent-3-yn-2-ol;

compound I-2 1-[2-chloro-4-(4-chlorophenoxy)phenyl]-1-cyclopropyl-2-(1,2,4-triazol-1-yl)ethanol;

compound I-3 2-[4-(4-chlorophenoxy)-2-(trifluoromethyl)phenyl]-1-(1,2,4-triazol-1-yl)propan-2-ol;

compound I-4 1-[4-(4-chlorophenoxy)-2-(trifluoromethyl)phenyl]-1-cyclopropyl-2-(1,2,4-triazol-1-yl)ethanol;

compound I-5 2-[4-(4-chlorophenoxy)-2-(trifluoromethyl)phenyl]-3-methyl-1-(1,2,4-triazol-1-yl)butan-2-ol;

compound I-6 1-[2-[2-chloro-4-(4-chlorophenoxy)phenyl]-2-methoxy-pent-3-ynyl]-1,2,4-triazole;

compound I-7 2-[4-(4-chlorophenoxy)-2-(trifluoromethyl)phenyl]-1-(1,2,4-triazol-1-yl)butan-2-ol;

compound I-8 1-[2-[2-chloro-4-(4-chlorophenoxy)phenyl]-2-cyclopropyl-2-methoxy-ethyl]-1,2,4-triazole;

compound I-9 1-[2-[4-(4-chlorophenoxy)-2-(trifluoromethyl)phenyl]-2-methoxy-propyl]-1,2,4-triazole;

compound I-10 2-[2-chloro-4-(4-chlorophenoxy)phenyl]-3,3-dimethyl-1-(1,2,4-triazol-1-yl)butan-2-ol, compound I-11 1-[2-[4-(4-chlorophenoxy)-2-(trifluoromethyl)phenyl]-2-cyclopropyl-2-methoxy-ethyl]-1,2,4-triazole;

compound I-12 1-[2-[2-chloro-4-(4-chlorophenoxy)phenyl]-2-methoxy-3,3-dimethyl-butyl]-1,2,4-triazole;

compound I-13 1-[2-[4-(4-chlorophenoxy)-2-(trifluoromethyl)phenyl]-2-methoxy-butyl]1,2,4-triazole;

compound I-14 2-[4-(4-chlorophenoxy)-2-(trifluoromethyl)phenyl]-1-(1,2,4-triazol-1-yl)pent-3-yn-2-ol;

compound I-15 1-[2-[4-(4-chlorophenoxy)-2-(trifluoromethyl)phenyl]-2-methoxy-pent-3-ynyl]-1,2,4-triazole;

compound I-16 2-[4-(4-chlorophenoxy)-2-(trifluoromethyl)phenyl]-1-(1,2,4-triazol-1-yl)but-3-yn-2-ol;

compound I-17 2-[2-chloro-4-(4-chlorophenoxy)phenyl]-1-(1,2,4-triazol-1-yl)propan-2-ol;

compound I-18 2-[2-chloro-4-(4-fluorophenoxy)phenyl]-1-(1,2,4-triazol-1-yl)propan-2-ol;

compound I-19 2-[2-chloro-4-(4-chlorophenoxy)phenyl]-3-methyl-1-(1,2,4-triazol-1-yl)butan-2-ol;

compound I-20 1-[2-[2-chloro-4-(4-chlorophenoxy)phenyl]-2-methoxy-propyl]-1,2,4-triazole;

compound I-21 1-[2-[2-chloro-4-(4-chlorophenoxy)phenyl]-2-methoxy-butyl]-1,2,4-triazole;

compound I-22 1-[2-[2-chloro-4-(4-chlorophenoxy)phenyl]-2-methoxy-pentyl]-1,2,4-triazole;

compound I-23 2-[2-chloro-4-(4-chlorophenoxy)phenyl]-1,1,1-trifluoro-3-(1,2,4-triazol-1-yl)propan-2-ol;

compound I-24 2-[2-chloro-4-(4-chlorophenoxy)phenyl]-3-fluoro-1-(1,2,4-triazol-1-yl)butan-2-ol hydrochloride;

compound I-25 2-[2-chloro-4-(4-chlorophenoxy)phenyl]-1-(1,2,4-triazol-1-yl)pent-4-yn-2-ol;

compound I-26 2-[2-chloro-4-(4-chlorophenoxy)phenyl]-1-methoxy-3-(1,2,4-triazol-1-yl)propan-2-ol;

compound I-27 2-[2-chloro-4-(4-fluorophenoxy)phenyl]-1-methoxy-3-(1,2,4-triazol-1-yl)propan-2-ol;

compound I-28 2-[4-(4-chlorophenoxy)-2-(trifluoromethyl)phenyl]-1-(1,2,4-triazol-1-yl)pentan-2-ol;

compound I-29 2-[4-(4-fluorophenoxy)-2-(trifluoromethyl)phenyl]-1-(1,2,4-triazol-1-yl)propan-2-ol;

compound I-30 2-[2-chloro-4-(4-chlorophenoxy)phenyl]-1-(1,2,4-triazol-1-yl)butan-2-ol; and compound I-31 2-[2-chloro-4-(4-chlorophenoxy)phenyl]-1-(1,2,4-triazol-1-yl)pentan-2-ol.

The structures of the compounds I-1 to I-31 are as follows:

I-1 2-[2-chloro-4-(4-chlorophenoxy)phenyl]-1-(1,2,4-triazol-1-yl)pent-3-yn-2-ol

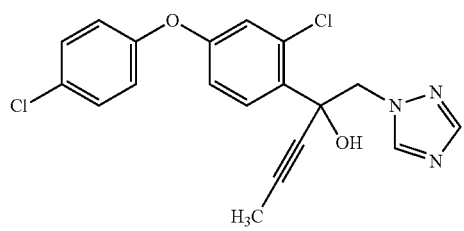

I-2 1-[2-chloro-4-(4-chlorophenoxy)phenyl]-1-cyclopropyl-2-(1,2,4-triazol-1-yl)ethanol

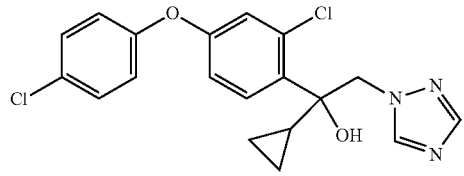 [SMILES: OC(Cn1cncn1)(c1ccc(Oc2ccc(Cl)cc2)cc1Cl)C1CC1]

I-3 2-[4-(4-chlorophenoxy)-2-(trifluoromethyl)phenyl]-1-(1,2,4-triazol-1-yl)propan-2-ol

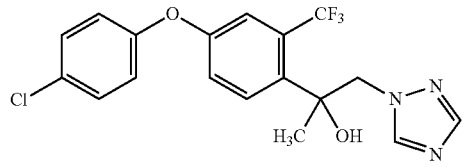

I-4 1-[4-(4-chlorophenoxy)-2-(trifluoromethyl)phenyl]-1-cyclopropyl-2-(1,2,4-triazol-1-yl)ethanol

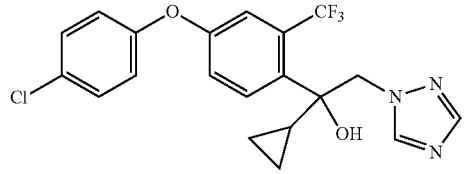 [SMILES: OC(Cn1cncn1)(c1ccc(Oc2ccc(Cl)cc2)cc1C(F)(F)F)C1CC1]

I-5 2-[4-(4-chlorophenoxy)-2-(trifluoromethyl)phenyl]-3-methyl-1-(1,2,4-triazol-1-yl)butan-2-ol

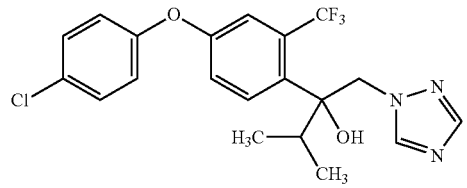 [SMILES: CC(C)C(O)(Cn1cncn1)c1ccc(Oc2ccc(Cl)cc2)cc1C(F)(F)F]

I-6 1-[2-[2-chloro-4-(4-chlorophenoxy)phenyl]-2-methoxy-pent-3-ynyl]-1,2,4-triazole

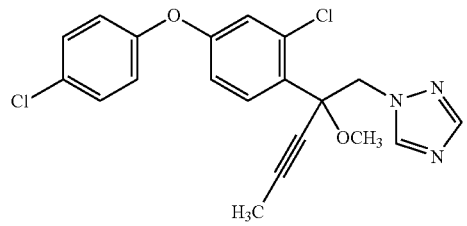 [SMILES: CC#CC(Cn1cncn1)(OC)c1ccc(Oc2ccc(Cl)cc2)cc1Cl]

I-7 2-[4-(4-chlorophenoxy)-2-(trifluoromethyl)phenyl]-1-(1,2,4-triazol-1-yl)butan-2-ol

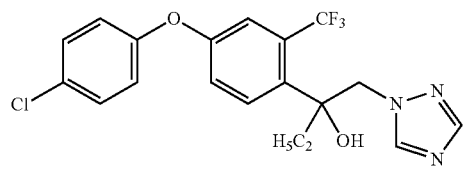

I-8 1-[2-[2-chloro-4-(4-chlorophenoxy)phenyl]-2-cyclopropyl-2-methoxy-ethyl]-1,2,4-triazole

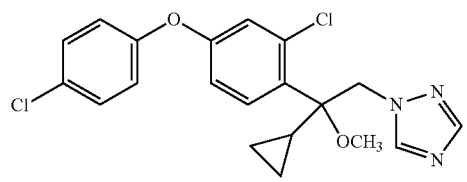 [SMILES: COC(Cn1cncn1)(c1ccc(Oc2ccc(Cl)cc2)cc1Cl)C1CC1]

I-9 1-[2-[4-(4-chlorophenoxy)-2-(trifluoromethyl)phenyl]-2-methoxy-propyl]-1,2,4-triazole

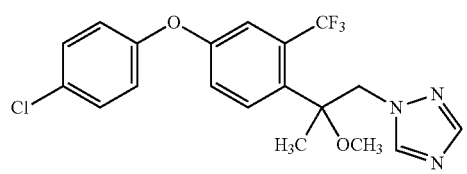 [SMILES: COC(C)(Cn1cncn1)c1ccc(Oc2ccc(Cl)cc2)cc1C(F)(F)F]

I-10 2-[2-chloro-4-(4-chlorophenoxy)phenyl]-3,3-dimethyl-1-(1,2,4-triazol-1-yl)butan-2-ol

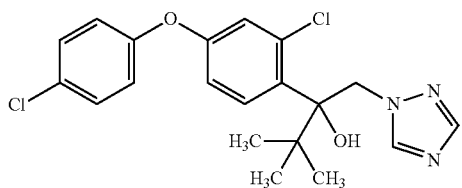 [SMILES: CC(C)(C)C(O)(Cn1cncn1)c1ccc(Oc2ccc(Cl)cc2)cc1Cl]

I-11 1-[2-[4-(4-chlorophenoxy)-2-(trifluoromethyl)phenyl]-2-cyclopropyl-2-methoxy-ethyl]-1,2,4-triazole

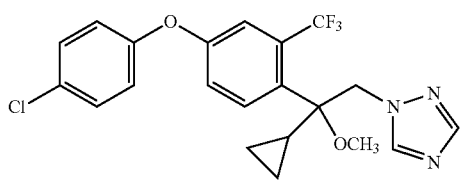 [SMILES: COC(Cn1cncn1)(c1ccc(Oc2ccc(Cl)cc2)cc1C(F)(F)F)C1CC1]

I-12 1-[2-[2-chloro-4-(4-chlorophenoxy)phenyl]-2-methoxy-3,3-dimethyl-butyl]-1,2,4-triazole

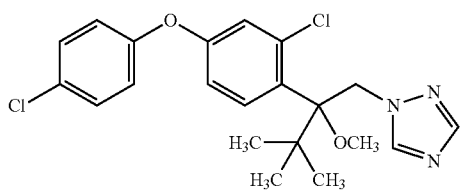 [SMILES: COC(Cn1cncn1)(c1ccc(Oc2ccc(Cl)cc2)cc1Cl)C(C)(C)C]

I-13 1-[2-[4-(4-chlorophenoxy)-2-(trifluoromethyl)phenyl]-2-methoxy-butyl]1,2,4-triazole

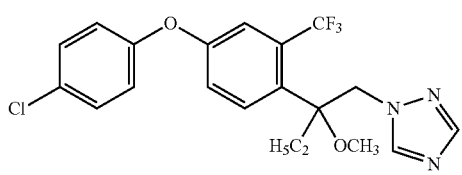

I-14 2-[4-(4-chlorophenoxy)-2-(trifluoromethyl)phenyl]-1-(1,2,4-triazol-1-yl)pent-3-yn-2-ol

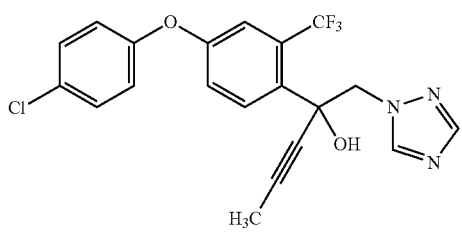 [SMILES: CC#CC(O)(Cn1cncn1)c1ccc(Oc2ccc(Cl)cc2)cc1C(F)(F)F]

I-15 1-[2-[4-(4-chlorophenoxy)-2-(trifluoromethyl)phenyl]-2-methoxy-pent-3-ynyl]-1,2,4-triazole

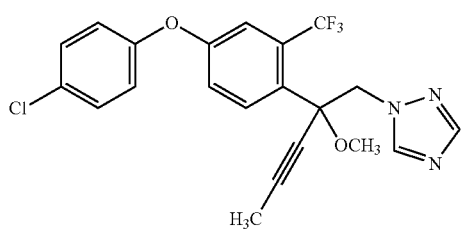 [SMILES: CC#CC(Cn1cncn1)(OC)c1ccc(Oc2ccc(Cl)cc2)cc1C(F)(F)F]

I-16 2-[4-(4-chlorophenoxy)-2-(trifluoromethyl)phenyl]-1-(1,2,4-triazol-1-yl)but-3-yn-2-ol

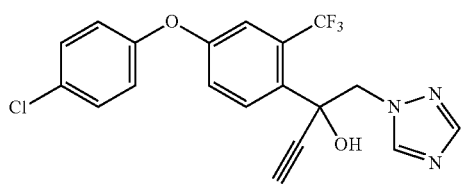 [SMILES: C#CC(O)(Cn1cncn1)c1ccc(Oc2ccc(Cl)cc2)cc1C(F)(F)F]

I-17 2-[2-chloro-4-(4-chlorophenoxy)phenyl]-1-(1,2,4-triazol-1-yl)propan-2-ol

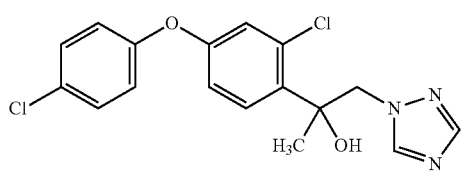

I-18 2-[2-chloro-4-(4-fluorophenoxy)phenyl]-1-(1,2,4-triazol-1-yl)propan-2-ol

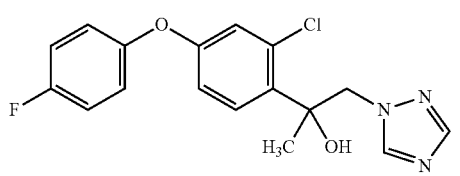 [SMILES: CC(O)(Cn1cncn1)c1ccc(Oc2ccc(F)cc2)cc1Cl]

I-19 2-[2-chloro-4-(4-chlorophenoxy)phenyl]-3-methyl-1-(1,2,4-triazol-1-yl)butan-2-ol

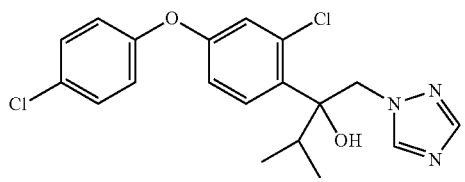 [SMILES: CC(C)C(O)(Cn1cncn1)c1ccc(Oc2ccc(Cl)cc2)cc1Cl]

I-20 1-[2-[2-chloro-4-(4-chlorophenoxy)phenyl]-2-methoxy-propyl]-1,2,4-triazole

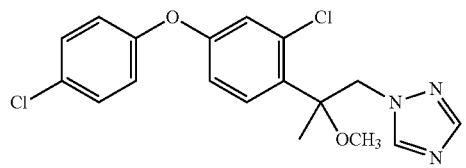 [SMILES: COC(C)(Cn1cncn1)c1ccc(Oc2ccc(Cl)cc2)cc1Cl]

I-21 1-[2-[2-chloro-4-(4-chlorophenoxy)phenyl]-2-methoxy-butyl]-1,2,4-triazole

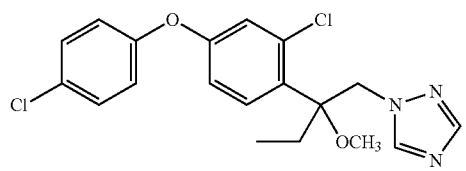 [SMILES: CCC(Cn1cncn1)(OC)c1ccc(Oc2ccc(Cl)cc2)cc1Cl]

I-22 1-[2-[2-chloro-4-(4-chlorophenoxy)phenyl]-2-methoxy-pentyl]-1,2,4-triazole

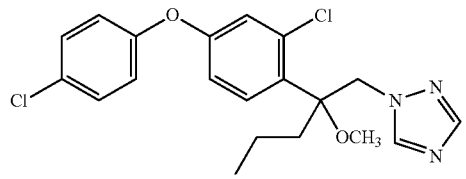 [SMILES: CCCC(Cn1cncn1)(OC)c1ccc(Oc2ccc(Cl)cc2)cc1Cl]

I-23 2-[2-chloro-4-(4-chlorophenoxy)phenyl]-1,1,1-trifluoro-3-(1,2,4-triazol-1-yl)propan-2-ol

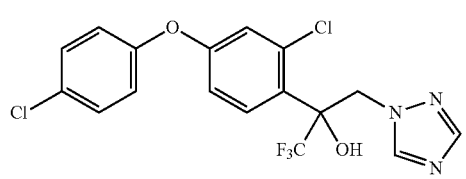 [SMILES: OC(Cn1cncn1)(c1ccc(Oc2ccc(Cl)cc2)cc1Cl)C(F)(F)F]

I-24 2-[2-chloro-4-(4-chlorophenoxy)phenyl]-3-fluoro-1-(1,2,4-triazol-1-yl)butan-2-ol hydrochloride

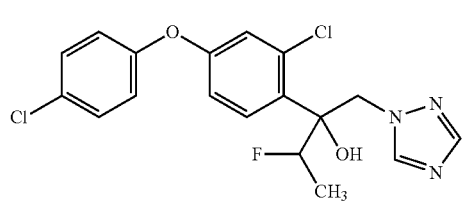 [SMILES: CC(F)C(O)(Cn1cncn1)c1ccc(Oc2ccc(Cl)cc2)cc1Cl]

I-25 2-[2-chloro-4-(4-chlorophenoxy)phenyl]-1-(1,2,4-triazol-1-yl)pent-4-yn-2-ol

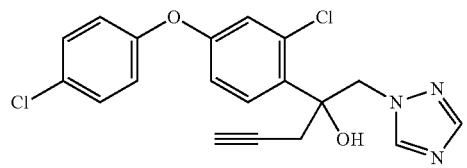 [SMILES: C#CCC(O)(Cn1cncn1)c1ccc(Oc2ccc(Cl)cc2)cc1Cl]

I-26 2-[2-chloro-4-(4-chlorophenoxy)phenyl]-1-methoxy-3-(1,2,4-triazol-1-yl)propan-2-ol

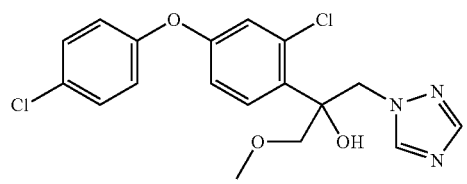 [SMILES: COCC(O)(Cn1cncn1)c1ccc(Oc2ccc(Cl)cc2)cc1Cl]

I-27 2-[2-chloro-4-(4-fluorophenoxy)phenyl]-1-methoxy-3-(1,2,4-triazol-1-yl)propan-2-ol

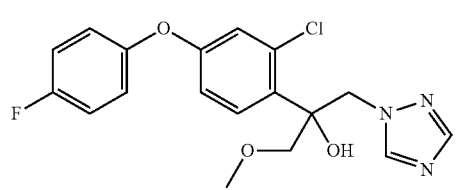 [SMILES: COCC(O)(Cn1cncn1)c1ccc(Oc2ccc(F)cc2)cc1Cl]

I-28 2-[4-(4-chlorophenoxy)-2-(trifluoromethyl)phenyl]-1-(1,2,4-triazol-1-yl)pentan-2-ol I-29 2-[4-(4-fluorophenoxy)-2-(trifluoromethyl)phenyl]-1-(1,2,4-triazol-1-yl)propan-2-ol

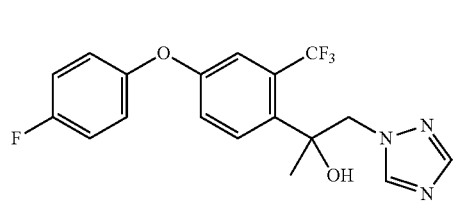 [SMILES: CC(O)(Cn1cncn1)c1ccc(Oc2ccc(F)cc2)cc1C(F)(F)F]

I-30 2-[2-chloro-4-(4-chlorophenoxy)phenyl]-1-(1,2,4-triazol-1-yl)butan-2-ol

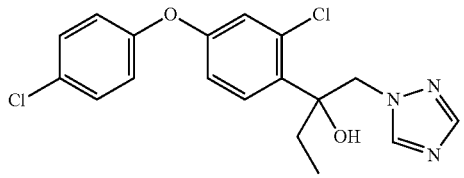 [SMILES: CCC(O)(Cn1cncn1)c1ccc(Oc2ccc(Cl)cc2)cc1Cl]

and

I-31 2-[2-chloro-4-(4-chlorophenoxy)phenyl]-1-(1,2,4-triazol-1-yl)pentan-2-ol

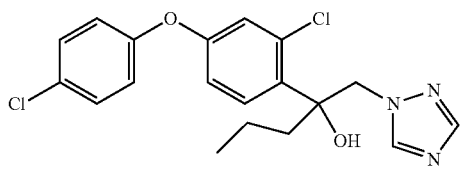

According to one particular embodiment of the invention, the pesticide is selected from the compounds I-1, I-2, I-3, I4, I-5, I-14, and I-19.

According to a further particular embodiment of the invention, the pesticide is selected from the compounds I-1, I-3, I-4, I-5 and I-19.

According to still a further particular embodiment of the invention, the pesticide is selected from the compounds I-1, I-3, I-5 and I-19.

According to still a further particular embodiment of the invention, the pesticide is selected from the compounds I-1, I-3 and I-5. In one embodiment, it is I-1, in a further embodiment, it is I-3. In still another embodiment, it is I-5.

The triazole fungicides of formula I, in particular I-1 to I-31, are known as fungicides. They can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2). Furthermore, the compounds of formula I, their preparation and use in crop protection are described in WO 2013/007767 (PCT/EP2012/063626), WO 2013/024076 (PCT/EP2012/065835), WO 2013/024075 (PCT/EP2012/065834), WO 2013/024077 (PCT/EP2012/065836), WO 2013/024081 (PCT/EP2012/065848), WO 2013/024080 (PCT/EP2012/065847), WO 2013/024083 (PCT/EP2012/065852), WO 2013/010862 (PCT/EP2012/063526), WO 2013/010894 (PCT/EP2012/063635), WO 2013/010885 (PCT/EP2012/063620), WO 2013/024082 (PCT/EP2012/065850), which also disclose certain compositions with other active compounds. Owing to the basic character of their nitrogen atoms, they are capable of forming salts or adducts with inorganic or organic acids or with metal ions, in particular salts with inorganic acids or N-oxides.

The compounds I comprise chiral centers and they may be obtained in the form of racemates. The R- and S-enantiomers of the triazole compounds can be separated and isolated in pure form with methods known by the skilled person, e.g. by using chiral HPLC. Suitable for use are both the enantiomers and compositions thereof. Furthermore, said compounds I can be present in different crystal modifications, which may differ in biological activity.

In particular, in each case, any proportions of the (R)-enantiomer and the (S)-enantiomer of the respective compound I-1, I-2, I-3, I-4, I-5, etc., respectively, may be present. For example, the (R)-enantiomer of compound I-3 is (R)-2-[4-(4-chlorophenoxy)-2-(trifluoromethyl)phenyl]-1-(1,2,4-triazol-1-yl)propan-2-ol; the (S)-enantiomer of I-3 is (S)-2-[4-(4-chlorophenoxy)-2-(trifluoromethyl)phenyl]-1-(1,2,4-triazol-1-yl)propan-2-ol. This applies to the other compounds accordingly.

The respective compound I-1, I-2, I-3, I-4 or I-5, respectively, etc., may be provided and used as (R)-enantiomer with an enantiomeric excess (e.e.), e.g. of at least 40%, for example, at least 50%, 60%, 70% or 80%, preferably at least 90%, more preferably at least 95%, yet more preferably at least 98% and most preferably at least 99%. According to a further specific embodiment, the respective compound I is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%. This applies to every composition detailed herein.

Furthermore, the pesticides that may be also used according to the invention, their preparation and their biological activity e.g. against harmful fungi, pests or weed is known (cf: http://www.alanwood.net/pesticides/); these substances are mostly commercially available.

According to a further embodiment, the pesticide is selected from the group of the Inhibitors of complex III at Qo site (e.g. strobilurins). In particular, the pesticide is selected from the group consisting of azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester, 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone and fenamidone.

According to still a further embodiment, the pesticide is selected from the group of the inhibitors of complex II (e.g. carboxamides). In particular, the pesticide is selected from the group consisting of benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethyl-indan-4-yl)pyrazole-4-carboxamide, 3-(trifluoromethyl)-1-methyl-N-(1,1,3-trimethyl-indan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide and N-[2-(2,4-dichlorophenyl)-2-methoxy-1-methyl-ethyl]-3-(difluoromethyl)-1-methyl-pyrazole-4-carboxamide.

In another form the pesticide comprises fluxapyroxad, difenoconazole, and propiconazole.

The pesticide is water-insoluble. Usually, it is soluble in water to not more than 1 g/l, preferably not more than 200 mg/l and in particular to not more than 50 mg/l at 25° C. Using simple preliminary experiments, the skilled worker can select a pesticide with a suitable water-solubility from the above pesticide list.

The pesticide can have a melting point of more than 40° C., preferably more than 70° C. and in particular more than 90 C.

The pesticide is preferably present in the concentrate in dissolved form. Using simple preliminary experiments, the skilled worker can select, from the above pesticide list, a pesticide with a suitable solubility.

In addition to the water-insoluble pesticide, the concentrate can comprise one or more further pesticides. The further pesticide is preferably water-insoluble. Usually, it is soluble in water to not more than 1 g/l, preferably not more than 200 mg/l and in particular not more than 50 mg/l at 25° C. Using simple preliminary experiments, the skilled worker can select a pesticide with a suitable water-solubility from the above pesticide list. In an especially preferred form, the concentrate does not comprise any further pesticide.

The concentrate may comprise from 0.1 to 60% by weight, preferably from 1 to 25% by weight, in particular from 5 to 15% by weight, of pesticide, the basis being the total of all the pesticides present in the concentrate.

The emulsifiable concentrate can furthermore comprise auxiliaries conventionally used for crop protection products. Suitable auxiliaries are solvents, liquid carriers, surfactants, dispersants, emulsifiers, wetters, adjuvants, solubilizers, penetrants, protective colloids, stickers, thickeners, bactericides, antifreeze agents, antifoam agents, colorants, adhesives and binders.

Suitable solvents and liquid carriers are organic solvents such as oils of vegetable or animal origin; alcohols, for example ethanol, propanol, butanol, cyclohexanol; glycols; ketones; esters; and their mixtures.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetrant, protective colloid, or auxiliary. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates. Preferred anionic surfactants are sulfates and sulfonates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsitiuted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate. Preferred nonionic surfactants are alkoxylates. Nonionic surfactants such as alkoxylates may also be employed as adjuvants.

Suitable cationic surfactants are quaternary surfactants, for example quaternary ammonium compounds with one or two hydrophobic groups, or salts of long-chain primary amines.

Suitable amphoteric surfactants are alkylbetains and imidazolines.

Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases, wherein polyacdis are preferred. Examples of polybases are polyvinylamines or polyethyleneamines. Examples of polyacids are acrylic acid copolymers, or AMPS (2-acrylamido-2-methylpropane sulfonic acid) copolymers. Preferred polyelectrolyte is a copolymer, which contains in polymerized form an amide containing at least one monomer selected from N-vinyllactam, N—$C_1$-$C_6$ alkyl acrylamide and N,N-di-$C_1$-$C_6$ alkyl acrylamide; a poly($C_{2\text{-}6}$alkylene glycol) (meth)acrylate and/or a mono $C_{1\text{-}22}$ alkyl terminated poly ($C_{2\text{-}6}$ alkylene glycol) (meth)acrylate; a $C_1$-$C_8$ alkyl (meth) acrylate; and (meth)acrylic acid. More preferred polyelectrolyte is a copolymer, which contains in polymerized form an amide containing at least one monomer selected from N-vinyllactam; a mono $C_{1\text{-}22}$ alkyl terminated poly($C_{2\text{-}6}$ alkylene glycol) (meth)acrylate; a $C_1$-$C_8$ alkyl (meth)acrylate; and (meth)acrylic acid. In another preferred form the polyelectrolyte is a copolymer, which contains in polymerized form 25 to 85 wt % of an amide containing at least one monomer selected from N-vinyllactam; 1 to 40 wt % of a mono $C_{1\text{-}22}$ alkyl terminated poly($C_{2\text{-}6}$ alkylene glycol) (meth)acrylate; 5 to 50 wt % of a $C_1$-$C_8$ alkyl (meth)acrylate; and up to 15 wt % of (meth)acrylic acid, wherein the sum of monomers equals 100%. In another preferred form the polyelectrolyte is a copolymer, which contains in polymerized form 30 to 85 wt % of an amide containing at least one monomer selected from N-vinyllactam; 5 to 20 wt % of a mono $C_{1\text{-}22}$ alkyl terminated poly($C_{1\text{-}6}$ alkylene glycol) (meth)acrylate; 8 to 35 wt % of a $C_1$-$C_8$ alkyl (meth)acrylate; and 0.5 to 10 wt % of (meth)acrylic acid, wherein the sum of monomers equals 100%. In another preferred form the polyelectrolyte is a copolymer, which contains in polymerized form at least one ethylenically unsaturated monomer containing sulfonic acid groups, at least one monomer selected from $C_1$-$C_4$ alkyl (meth)acrylates, and at least one monomer selected from $C_6$-$C_{22}$ alkyl (meth)acrylates. In another preferred form the polyelectrolyte is a copolymer, which contains in polymerized form 5% to 50% by weight of at least one ethylenically unsaturated monomer containing sulfonic acid groups, 20% to 70% by weight of at least one monomer selected from $C_1$-$C_4$ alkyl (meth)acrylates, and 5% to 30% by weight of at least one monomer selected from $C_6$-$C_{22}$ alkyl (meth)acrylates, based on the total weight of the monomers. The concentrate may comprise from 0.5 to 40% by weight, preferably from 2 to 30% by weight, and in particular from 5 to 25% by weight of the polyelectrolye (e.g. the polyacid, like acrylic acid copolymers, or AMPS copolymers).

Suitable adjuvants are compounds which have negligible or even no pesticidal activity themselves, and which improve the biological performance of the pesticide on the target. Examples are surfactants, mineral or vegetable oils, and other auxilaries. Further examples are listed by Knowles, Adjuvants and Additives, Agrow Reports DS256, T&F Informa UK, 2006, chapter 5.

Suitable bactericides are bronopol and isothiazolinone derivatives such as alkylisothiazolinones and benzisothiazolinones. Suitable antifreeze agents are ethylene glycol, propylene glycol, urea and glycerol. Suitable antifoam agents are silicones, long-chain alcohols, and salts of fatty acids. Suitable colorants (e.g. in red, blue, or green) are pigments which are sparingly soluble in water, and water-soluble dyes. Examples are inorganic colorants (e.g. iron oxide, titanium oxide, iron hexacyanoferrate) and organic colorants (e.g. alizarin, azo and phthalocyanine colorants).

The concentrate preferably comprises at least one anionic surfactant. The concentrate usually comprises not less than 0.03% by weight of anionic surfactants, preferably not less than 0.1% by weight and in particular not less than 0.5% by weight. The composition can comprise not more than 25% by weight of anionic surfactants, preferably not more than 10% by weight and in particular not more than 5% by weight.

The concentrate preferably comprises at least one non-ionic surfactant (such as alkoxylates). The concentrate usually comprises not less than 1% by weight of nonionic surfactants, preferably not less than 5% by weight and in particular not less than 10% by weight. The composition can comprise not more than 65% by weight of nonionic surfactants, preferably not more than 45% by weight and in particular not more than 35% by weight.

In a preferred form, the concentrate preferably comprises at least one alkoxylate, in particular an alkoxylated $C_6$-$C_{22}$-alcohol. The concentrate usually comprises not less than 2% by weight of alkoxylates (in particular an alkoxylated $C_6$-$C_{22}$-alcohol), preferably not less than 7% by weight and in particular not less than 10% by weight.

Preferably, the concentrate comprises a nonionic surfactant (such as alkoxylates) and an anionic surfactant (such as sulfates or sulfonates).

The invention furthermore relates to a process for the preparation of the emulsifiable concentrate according to the invention by mixing the water-insoluble pesticide, the amide of the formula (I), the lactamide of the formula (II), and optionally the hydrocarbon.

The invention furthermore relates to an emulsifiable concentrate comprising the water-insoluble pesticides fluxapyroxad, difenoconazole, and propiconazole. The concentrate may comprise further pesticides in addition to these three pesticides. The emulsifiable concentrate may comprise 5 to 300 g/l (preferably 15 to 200 g/l) fluxapyroxad, 30 to 500 g/l (preferably 100 to 350 g/l) difenoconazole, and 30 to 500 g/l (preferably 100 to 350 g/l) propiconazole. The emulsifiable concentrate comprising fluxapyroxad, difenoconazole, and propiconazole may further comprise auxiliaries conventionally used for crop protection products. The emulsifiable concentrate comprising fluxapyroxad, difenoconazole, and propiconazole may further comprise the amide of the formula (I) and the lactamide of the formula (II). The emulsifiable concentrate comprising fluxapyroxad, difenoconazole, and propiconazole may have preferred features as those disclosed for the emulsifiable concentrate comprising the water-insoluble pesticide, the amide of the formula (I) and the lactamide of the formula (II).

The invention furthermore relates to an emulsion obtainable (preferably obtained) by mixing water and the emulsifiable concentrate according to the invention. The emulsion normally arises spontaneously upon mixing. In most cases, the emulsion is an oil-in-water emulsion. The mixing ratio of water to concentrate can be in the range of from 1000 to 1 up to 1 to 1, preferably 200 to 1 up to 3 to 1.

The invention furthermore relates to a method for controlling phytopathogenic fungi and/or undesired vegetation and/or undesired attack by insects or mites and/or for regulating the growth of plants, where the concentrate according to the invention or the emulsion according to the invention is allowed to act on the respective pests, their environment or on the crop plants to be protected from the respective pests, on the soil and/or on undesired plants and/or on the crop plants and/or their environment. In general, the therapeutic treatment of humans and animals is excluded from the method for controlling phytopathogenic fungi and/or undesired vegetation and/or undesired attack by insects or mites and/or for regulating the growth of plants.

When employed in crop protection, the application rates of the pesticides amount to from 0.001 to 2 kg per ha, preferably from 0.005 to 2 kg per ha, especially preferably from 0.05 to 0.9 kg per ha and in particular from 0.1 to 0.75 kg per ha, depending on the nature of the desired effect. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kg of plant propagation material (preferably seed) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizers or micronutrients and further pesticides (for example herbicides, insecticides, fungicides, growth regulators, safeners) may be added to the emulsion in the form of a premix or optionally only shortly before use (tank mix). These agents can be admixed to the compositions according to the invention at a weight ratio of from 1:100 to 100:1, preferably from 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

Advantages of the present invention are, inter alia, that the concentrate is highly stable to low temperatures (e.g. even below 0° C.); that the pesticide does not precipitate, cream or crystallize in the concentrate at low temperatures (e.g. even below 0° C.); that the pesticide does not precipitate, cream or crystallize in the emulsion obtained from the concentrate, e.g. at low temperatures (e.g. even below 0° C.); that high pesticide concentrations in the concentrate can be employed; that an emulsion forms spontaneously upon dilution of the concentrate with water; that the concentrate is capable of being stored over prolonged periods; that the concentrate does not require the presence of water (e.g. because it might freeze below 0° C. or would favor bacterial growth during storage); that the concentrate forms a stable emulsion upon dilution with water; that adjuvants (such as alcohol alkoxylates) can be included in the concentrate formulations, e.g. even in high concentrations; that the pesticide in the emulsion obtained from the concentrate does not clog any spraying filters or nozzles, e.g. at low temperatures, or when diluted with hard water.

The examples which follow illustrate the invention without imposing any limitation.

EXAMPLES

Pesticide A: 2-[4-(4-chlorophenoxy)-2-(trifluoromethyl)phenyl]-1-(1,2,4-triazol-1-yl)propan-2-ol Lactamide A: N,N-dimethyl lactamide Fatty Amide A: N,N-dimethyldecanamide Hydrocarbon: Aromatic hydrocarbons mixture, distillation range 235-300° C., freezing point below −5° C., aromatic content about 99 wt %.

NS1: liquid, water-soluble nonionic surfactant ethoxylated castor oil

NS2: water-soluble nonionic surfactant, liquid alkoxylated fatty alcohol, surface tension (1 g/l at 23° C.) about 30 mN/m NS3: nonionic surfactant, liquid ethoxylated and propoxylated alcohol, solidifaction point about −7° C., dynamic viscosity (23° C.) about 120 mPas NS4: nonionic surfactant, liquid ethoxylated polyalkylarylphenol, HLB 12-13

NS5: nonionic surfactant, ethoxylated castor oil.

AS1: anionic surfactant calcium alkylbenzenesulfonate

AS2: anionic surfactant, 40 wt % iso-$C_{12}$ alkyl benzene sulfonate calcium salt in hydrocarbon solvent Polymer A: Copolymer prepared by radical polymerization, comprising a monomer mixture of 38 wt % vinylpyrrolidone, 29 wt % methyl methacrylate, 20 wt % tert-butyl acrylate, 3 wt % methacrylic acid, and 10 wt % $C_{16/18}$ alkyl terminated polyethylene glycol (25 EO) methacrylate.

Example 1

The emulsifiable concentrates of Pesticide A (each 100 g/l) were prepared by mixing the components as indicated in Table 1 (where each composition contained 10 AS1 and 40 g/l NS1) and filling up to a total volume of 1.0 l with Fatty Amide A. The compositions were clear solutions and are summarized in Table 1.

TABLE 1

| Composition (all data in g/l) | | | | | |
|---|---|---|---|---|---|
| | A | B | C | D | E |
| NS3 | 100 | 100 | 100 | 200 | 150 |
| NS2 | 100 | 100 | 100 | 50 | 50 |
| Lactamide A | 50 | 50 | 100 | 50 | 50 |
| Polymer A | 75 | 50 | 50 | 100 | 100 |
| Hydrocarbon | 200 | 100 | 100 | 100 | 100 |
| Active Solubility | Dissolved | Dissolved | Dissolved | Dissolved | Dissolved |

TABLE 1-continued

| Composition (all data in g/l) | | | | | |
|---|---|---|---|---|---|
| | A | B | C | D | E |
| Applicability | Free | Free | Free | Free | Free |
| Cold Stability | Stable | Stable | Stable | Stable | Stable |

Test for "Cold Stability"

One liter of each prepared EC formulation was placed in a refrigerator at −10° C. After 3 days storage in the refrigerator, the formulations were seeded with the respective pesticide crystals (less than 0.1 g/l). Twelve days after seeding the samples were observed for the crystallization of pesticide. Samples which did not show any crystals other than the added seed crystals were marked "Stable". Samples which showed crystals other than the added seed crystals were marked "Crystals".

Test for "Active Solubility"

One liter of each formulation was stored at room temperature for four hours after preparation. The formulations were seeded with the respective pesticide crystals (less than 0.1 g/l). The samples were observed for crystallization 24 hours after seeding. Samples which did not show any crystals other than the added seed crystals were marked "Dissolved". Samples which showed crystals other than the added seed crystals were marked "Crystals".

Test for "Applicability"

The test below was used to investigate whether the emulsifiable concentrates, following dilution to a sprayable concentration, can be used in standard sprayers without clogging the filters of the spraying machine or the spraying nozzles.

The test machine was a hydraulic sprayer with a 195 l tank, a four-piston membrane pump (at 3 bar pressure) and a spraying lance with 6 standard nozzles (type: LU 90-03). Nozzle filters used were four mesh filters (25, 50, 60, and 80 mesh), a 60-mesh mesh filter with integrated seal, and a 25-mesh slot filter. The suction filter and the pressure filter were each 50-mesh mesh filters.

The tank was first filled with 75 l of water and thereafter one liter of an emulsifiable concentrate. The mixture was mixed with a piston pump (stirring intensity: about 45 l/min) and subsequently the tank was filled up with a further 75 l of water. After pumped circulation for 120 minutes (stirring intensity: about 45 l/min) of the product mixture, the spray solution was sprayed out of the tank through the nozzles. During the test, the temperature of the spray mixture in the tank was kept constant at between 5 and 10° C. in order to simulate cold well water. The delivery test was repeated 4 times without cleaning the instruments between each application.

After 120 minutes of circulation, last filling ($4^{th}$) was left in the tank for additional 16 hours without stirring. After the standing time, the mixture was circulated additional 30 minutes, and then sprayed.

At the end of this procedure, the filters ahead of and downstream of the pump (suction filter 10 and pressure filter) and the filters in the nozzles (nozzle filters) were examined for residues.

In the tables "clogged" means that at least one of the filters (suction, pressure or nozzle filters) showed significant fouling, causing a reduction in flow or clogging. "Free" in the table means that no significant fouling was found, and "-" means that the sample was not tested.

Example 2

The emulsifiable concentrates of Pesticide A (each 100 g/l) were prepared by mixing the components as indicated in Table 2 (where each composition contained 10 g/l AS1, 40 g/l NS1, 50 g/l NS2, 200 g/l NS3, and 100 g/l Polymer A). Sample D corresponds to Sample D of Example 1. The samples were tested for "Active Solubility", "Applicability" and "Cold Stability" as described in Example 1.

TABLE 2

| | Composition (all data in g/l) | | | |
|---|---|---|---|---|
| | D | Comp A [a] | Comp B [a] | Comp C [a] |
| Lactamide A | 50 | — | Ad 1.0 L | 50 |
| Fatty Amide A | Ad 1.0 L | Ad 1.0 L | — | — |
| Hydrocarbon | 100 | 100 | 100 | Ad 1.0 L |
| Active Solubility | Dissolved | Dissolved | Dissolved | Crystals |
| Applicability | Free | Free | Clogged | — |
| Cold Stability | Stable | Crystals | Stable | — |

[a] not according to the invention

Example 3

The emulsifiable concentrates of Pesticide A (each 100 g/l), fluxapyroxad (each 50 g/l), and pyraclostrobin (each 100 g/l) were prepared by mixing the components as indicated in Table 3 (where each composition contained 10 g/l AS1 and 40 g/l NS1). The samples were tested for "Active Solubility", "Applicability" and "Cold Stability" as described in Example 1.

TABLE 3

| | Composition (all data in g/l) | | |
|---|---|---|---|
| | A | Comp A [a] | Comp B [a] |
| NS3 | 150 | 150 | 150 |
| NS2 | 50 | 50 | 50 |
| Lactamide A | 50 | — | 50 |
| Fatty Amide A | Ad 1.0 L | Ad 1.0 L | — |
| Hydrocarbon | 100 | 100 | Ad 1.0 L |
| Active Solubility | Dissolved | Dissolved | Crystals |
| Applicability | Free | Free | — |
| Cold Stability | Stable | Crystals | — |

[a] not according to the invention

Example 4

The emulsifiable concentrates of fluxapyroxad (each 30 g/l), pyraclostrobin (each 200 g/l) and propiconazole (each 125 g/l) were prepared by mixing the components and filling up to a total volume of 1.0 l with Hydrocarbon as indicated in Table 4. The samples were tested for "Active Solubility", "Applicability" and "Cold Stability" as described in Example 1.

TABLE 4

| | Composition (all data in g/l) | | | |
|---|---|---|---|---|
| | A | B | C | D |
| Lactamide A | 50 | 50 | 50 | 50 |
| Fatty Amide A | 150 | 150 | 150 | 150 |
| AS1 | 10 | 10 | — | — |
| NS1 | 40 | 40 | — | — |
| NS2 | 150 | 150 | 100 | — |
| NS3 | 150 | 150 | 100 | 150 |
| NS4 | — | — | 100 | 100 |
| NS5 | — | — | 100 | 100 |
| Applicability | Free | Free | Free | Free |
| Cold Stability | Stable | Stable | Stable | Stable |
| Active Solubility | Dissolved | Dissolved | Dissolved | Dissolved |

Example 5

The emulsifiable concentrates of fluxapyroxad (each 67 g/l), pyraclostrobin (each 133 g/l) and difenoconazole (each 100 g/l) were prepared by mixing the components as indicated in Table 5. The samples were tested for "Active Solubility", "Applicability" and "Cold Stability" as described in Example 1.

TABLE 5

| | Composition (all data in g/l) | |
|---|---|---|
| | A | B |
| Lactamide A | 50 | 50 |
| Fatty Amide A | 200 | Ad 1.0 L |
| Hydrocarbon | Ad 1.0 L | 150 |
| Polymer A | — | 75 |
| NS2 | — | 200 |
| NS3 | 200 | — |
| NS4 | 50 | 30 |
| NS5 | — | 40 |
| AS2 | 50 | — |
| Applicability | Free | Free |
| Cold Stability | Stable | Stable |
| Active Solubility | Dissolved | Dissolved |

Example 6

The emulsifiable concentrates of Pesticide A (each 100 g/l) and propiconazole (each 125 g/l) were prepared by mixing the components and filling up to a total volume of 1.0 L with Hydrocarbon as indicated in Table 6. The samples were tested for "Active Solubility", "Applicability" and "Cold Stability" as described in Example 1.

TABLE 6

| | Composition (all data in g/l) |
|---|---|
| | A |
| Lactamide A | 50 |
| Fatty Amide A | 150 |
| NS1 | 40 |
| NS3 | 200 |
| AS1 | 10 |
| Applicability | Free |
| Cold Stability | Stable |
| Active Solubility | Dissolved |

Example 7

The emulsifiable concentrate of fluxapyroxad (40 g/l), pyraclostrobin (266.6 g/l) and propiconazole (166.6 g/l) was prepared by mixing the components as indicated in Table 7 and 75 g/l Polymer A, and filling up to a total volume of 1.0 l with Hydrocarbon. The compositions are summarized in Table 7. The samples were tested for "Applicability" and "Cold Stability" as described in Example 1.

TABLE 7

| Composition (all data in g/l) | |
| --- | --- |
| | A |
| NS2 | 200 |
| NS4 | 30 |
| NS5 | 40 |
| Lactamide A | 50 |
| Fatty Amide A | 175 |
| Applicability | Free |
| Cold Stability | Stable |

Example 8

The emulsifiable concentrate of fluxapyroxad (60 g/l), difenoconazole (250 g/l) and propiconazole (250 g/l) was prepared by mixing the components and filling up to a total volume of 1.0 l with Hydrocarbon. The compositions are summarized in Table 8. The samples were tested for "Applicability" and "Cold Stability" as described in Example 1.

TABLE 8

| Composition (all data in g/l) | |
| --- | --- |
| | A |
| NS2 | 50 |
| NS4 | 30 |
| NS5 | 40 |
| Lactamide A | 50 |
| Fatty Amide A | 150 |
| Applicability | Free |
| Cold Stability | Stable |

We claim:

1. An emulsifiable concentrate comprising a water-insoluble pesticide,
an amide of the formula (I)

$$R^1\text{—}C(O)N(R^2)_2 \qquad (I)$$

where $R^1$ is $-C_5\text{-}C_{19}$-alkyl and $R^2$ is methyl, ethyl, propyl, butyl, or mixtures thereof;

and a lactamide of the formula (II)

$$H_3C\text{—}CH(OH)\text{—}C(O)N(R^3)_2 \qquad (II)$$

where $R^3$ is methyl, ethyl, propyl, butyl, or mixtures thereof, wherein the water-insoluble pesticide is soluble in water to not more than 1 g/l, the concentrate comprises from 15 to 65% by weight of the amide of the formula (I), 1 to 30% by weight of the lactamide of the formula (II), and optionally 5 to 40% by weight of the hydrocarbon, wherein the amounts of these components add up to a sum of 16 to 90% by weight and wherein the weight ratio of amide (I) to lactamide (II) is from 2:1 to 15:1.

2. The concentrate according to claim 1, where $R^1$ is a $C_8\text{-}C_{14}$ alkyl.

3. The concentrate according to claim 1, where $R^1$ is a $C_7\text{-}C_{13}$ alkyl.

4. The concentrate according to claim 1, where $R^2$ in formula (I) is methyl.

5. The concentrate according to claim 1, where $R^3$ in formula (II) is methyl.

6. The concentrate according to claim 1, further comprising a hydrocarbon.

7. The concentrate according to claim 6, comprising 2 to 45% by weight of the hydrocarbon.

8. The concentrate according to claim 1, where the weight ratio of the amide of the formula (I) to the lactamide of the formula (II) is in the range from 3:1 to 13:1.

9. The emulsifiable concentrate of claim 1, wherein water-insoluble pesticide is fluxapyroxad, difenoconazole, or propiconazole.

10. A process for the preparation of the concentrate according to claim 1 by mixing the water-insoluble pesticide, the amide of the formula (I), the lactamide of the formula (II), and optionally the hydrocarbon.

11. An emulsion obtainable by mixing water and the emulsifiable concentrate as defined in claim 1.

12. A method for controlling phytopathogenic fungi and/or undesired vegetation and/or undesired attack by insects or mites and/or for regulating the growth of plants, where a composition comprising the concentrate according to claim 1 is allowed to act on the respective pests, their environment or on the crop plants to be protected from the respective pests, on the soil and/or on undesired plants and/or on the crop plants and/or their environment.

13. The method of claim 12, wherein $R^1$ is a $C_8\text{-}C_{14}$ alkyl.

* * * * *